United States Patent
Berezhnyy et al.

(10) Patent No.: US 10,076,281 B2
(45) Date of Patent: Sep. 18, 2018

(54) DEVICE AND METHOD FOR SLEEP MONITORING

(71) Applicant: KONINKLIJKE PHILIPS N.V., Eindhoven (NL)

(72) Inventors: Igor Berezhnyy, Eindhoven (NL); Erik Gosuinus Petrus Schuijers, Eindhoven (NL); Pedro Miguel Fonseca, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/654,975

(22) PCT Filed: Nov. 27, 2014

(86) PCT No.: PCT/EP2014/075726
§ 371 (c)(1),
(2) Date: Jun. 23, 2015

(87) PCT Pub. No.: WO2015/078940
PCT Pub. Date: Jun. 4, 2015

(65) Prior Publication Data
US 2015/0351693 A1    Dec. 10, 2015

(30) Foreign Application Priority Data

Nov. 28, 2013    (EP) ..................................... 13194869

(51) Int. Cl.
*A61B 5/02*    (2006.01)
*A61B 5/00*    (2006.01)
(Continued)

(52) U.S. Cl.
CPC ............ *A61B 5/6892* (2013.01); *A61B 5/024* (2013.01); *A61B 5/0816* (2013.01);
(Continued)

(58) Field of Classification Search
CPC ......... A61B 5/00; A61B 5/0004; A61B 5/002; A61B 5/0022; A61B 5/0024;
(Continued)

(56) References Cited

U.S. PATENT DOCUMENTS 4,926,866 A * 5/1990 Lee ...................... A61B 5/1102
                                                          600/301
6,280,392 B1  8/2001 Yoshimi
(Continued)

FOREIGN PATENT DOCUMENTS

EP    1639941 A1    3/2006
EP    2301429 A1    3/2011
(Continued)

OTHER PUBLICATIONS

Joeseok Shim and Yujin Lim, "Implementation of Real Time Alert System Over Cloud Computing", International Journal of Energy, Information and Communication, vol. 4, Issue 3, Jun. 2013, pp. 37-44.

*Primary Examiner* — Christopher D Koharski
*Assistant Examiner* — Elizabeth K So

(57) ABSTRACT

A sleep monitoring device (100) is disclosed for measuring a biophysical variable (131) of a living-being (150), comprising at least two pressure sensors (101-103) spatially arranged in a predefined planar geometry. The living-being rests on the supporting layer (199) contacted by the sensors that generate sensor signals in response to pressure caused by the living being via the supporting layer. A processing unit (110) determines the position of the living-being on the supporting layer based on differences between the sensor signals; a magnitude attenuation factor is determined based on the position of the living-being and a position of a sensor; the biophysical variable is determined from a sensor signal generated by that sensor, including a magnitude correction based on the magnitude attenuation factor. The effect of the
(Continued)

invention is that only few sensors are needed to measure a biophysical variable accurately, irrespective of the living-being's position on the supporting layer.

15 Claims, 12 Drawing Sheets

(51) Int. Cl.
| | |
|---|---|
| *A61B 5/08* | (2006.01) |
| *A61B 5/024* | (2006.01) |
| *A61B 5/103* | (2006.01) |
| *A61B 5/11* | (2006.01) |
| *A61B 5/113* | (2006.01) |

(52) U.S. Cl.
CPC .......... *A61B 5/1036* (2013.01); *A61B 5/1102* (2013.01); *A61B 5/113* (2013.01); *A61B 5/1113* (2013.01); *A61B 5/1116* (2013.01); *A61B 5/4806* (2013.01); *A61B 5/4812* (2013.01); *A61B 5/72* (2013.01); *A61B 5/7278* (2013.01); *A61B 2503/04* (2013.01); *A61B 2503/12* (2013.01); *A61B 2503/40* (2013.01); *A61B 2562/0219* (2013.01); *A61B 2562/0247* (2013.01); *A61B 2562/046* (2013.01)

(58) Field of Classification Search
CPC ... A61B 5/0026; A61B 5/0028; A61B 5/0033; A61B 5/0048; A61B 5/0057; A61B 5/0062; A61B 5/0064; A61B 5/015; A61B 5/02; A61B 5/022; A61B 5/02208; A61B 5/02216; A61B 5/02225; A61B 5/0225; A61B 5/02255; A61B 5/023; A61B 5/024; A61B 5/02438; A61B 5/02444; A61B 5/0245; A61B 5/0255; A61B 5/03; A61B 5/04; A61B 5/0408; A61B 5/04087; A61B 5/0428; A61B 5/432; A61B 5/044; A61B 5/053; A61B 5/0555; A61B 5/103; A61B 5/107; A61B 5/1071; A61B 5/1072; A61B 5/1073; A61B 5/1075

See application file for complete search history.

(56) References Cited

U.S. PATENT DOCUMENTS

| | | |
|---|---|---|
| 2011/0224510 A1 | 9/2011 | Oakhill |
| 2012/0302842 A1 | 11/2012 | Kurtz |

FOREIGN PATENT DOCUMENTS

| | | |
|---|---|---|
| WO | 2010048112 A1 | 4/2010 |
| WO | 2011008175 A1 | 1/2011 |
| WO | 2012095783 A1 | 7/2012 |
| WO | 2013179189 A1 | 12/2013 |

* cited by examiner

DEVICE AND METHOD FOR SLEEP MONITORING

This application is the U.S. National Phase application under 35 U.S.C. § 371 of International Application No. PCT/EP2014/075726, filed on Nov. 27, 2014, which claims the benefit of European Application No. 13194869.7 filed on Nov. 28, 2013. These applications are hereby incorporated by reference herein.

FIELD OF THE INVENTION

The invention relates to a sleep monitoring device and method for measuring of biophysical signals of living-being resting on a mattress. Biophysical variables are extracted from the biophysical signals. The person's sleep state is inferred from the biophysical variables.

BACKGROUND OF THE INVENTION

U.S. Pat. No. 6,280,392 describes a sensor sheet having a grid of multiple load cells placed under (contacted by) an infant to be monitored. The sensor sheet is part of an infant condition monitoring system for monitoring the health condition of a sleeping infant without disturbing. An infant breathing signal is formed from load signals of the load cells, from which a breathing condition is determined. In addition, other biophysical signals such as body movements and weight are measured also from the load signals.

Said document describes the sensor sheet having a high spatial density of load cells, so that the infant's posture can be inferred by measuring pressure caused by the infant at various parts of the infant's body. Furthermore, having the high spatial density of load cells, there are multiple load cells contacting the infant, providing respective multiple load signals from which the infant breathing signal and other biophysical signals can be measured.

WO 2011/008175 A1 describes a method for patient monitoring using an array of pressure sensors. The method comprises the steps of: determining a value of a selection parameter of each pressure sensor of the array; selecting one or more of the pressure sensors based on the respective values of the selection parameter; and measuring a vital sign of the patient based on data obtained from said one or more selected pressure sensors.

SUMMARY OF THE INVENTION

The sensor sheet of the prior art is typically placed on a bed covering the surface of a bed. A disadvantage of the prior art is therefore that it requires many load cells sensors in order to contact the infant at any position on the bed. Hence, many load cells are required to measure a biophysical signal of the infant regardless of the infant's position on the bed.

It is an object of the invention to overcome the disadvantages of the prior art by providing a sleep monitoring device that uses only few sensors to measure sleep-related biophysical variables of an infant accurately regardless of the infant's position on the bed.

Disclosed is a sleep monitoring device for measuring a biophysical variable of a living-being, the device comprising sensors being at least two pressure sensors that are spatially arranged in a predefined planar geometry, the sensors being arranged for contacting a supporting layer for supporting the living-being while resting and generating respective sensor signals in response to pressure caused by the living-being via the supporting layer to the sensors, the sleep monitoring device comprising a processing unit arranged for performing: (a) a localization function configured for determining a position of the living-being on the supporting layer relative to the sensors based on differences between the respective sensor signals by performing a multilateration procedure based on phase differences between the respective sensor signals or by performing a trilateration procedure based on magnitude differences between the respective sensor signals, and (b) a determining function configured for determining a magnitude attenuation factor based on the determined position of the living-being and a position of one of the sensors, and determining the biophysical variable based on a sensor signal generated by the one of the sensors and the magnitude attenuation factor.

The sleep monitoring device measures a biophysical variable that characterizes a corresponding biophysical condition of the living-being, while the living-being is resting on a supporting layer. The living-being may be an infant, an human adult or even an animal. For example, the sleep monitoring device measures a breathing rate and breathing intensity that characterize the breathing condition of an infant lying on a mattress.

Each of the sensors responds to pressure caused by the living-being via the supporting layer by generating a sensor signal. The sensors are spatially arranged in a predefined geometry so that positions of the sensors relative to one another are fixed and known to the sleep monitoring device. Furthermore, the predefined geometry is planar to allowing fitting of the sensors in the layer, the layer itself having a flat shape by definition.

The processing unit determines the biophysical variable of the living-being while taking into account the position of the living-being relative to the sensors. Sensors are at different positions on the supporting layer and, consequently, the distance between a sensor and the position of the living-being is different for each sensor. A pressure wave caused by the living-being propagates through the supporting layer over the distance from the living-being to the sensor and is attenuated by an amount that increases with the distance. When the living-being causes a pressure wave, each sensor senses the pressure wave but attenuated by a different amount. In response, each sensor generates a sensor signal with a different magnitude.

The processing unit determines the biophysical variable from the sensor signals using the localization function and the determining function.

The localization function determines the position of the living-being (relative to the sensors) based on the differences between the sensor signals. Namely, the localization function computes said position from differences between the sensor signals by performing a multilateration procedure based on phase differences or by performing a trilateration procedure based on magnitude differences.

The determining function determines a magnitude attenuation factor reflecting the attenuation of pressure propagating from the position of the living-being (determined by the localization function) to the position of the sensor. The determining function then determines the biophysical variable from the sensor signal, including a correction based on the magnitude attenuation factor. For example, a magnitude of a sensor signal is corrected using the magnitude attenuation factor, a biophysical signal (e.g. a breathing signal) is filtered from the corrected sensor signal, and the biophysical variable is extracted from the biophysical signal. Or, as variation to the previous example, a biophysical signal is extracted from the sensor signal, the magnitude of the biophysical signal is corrected using the magnitude attenuation factor, and the biophysical variable is extracted from the corrected biophysical signal.

Also disclosed is a method for measuring a biophysical variable of a living-being, using sensors being at least two pressure sensors that are spatially arranged in a predefined planar geometry, the sensors being arranged for contacting a supporting layer for supporting the living-being while resting and generating respective sensor signals in response to pressure caused by the living-being via the supporting layer to the sensors, the method comprising the steps of: determining a position of the living-being on the supporting layer relative to the sensors based on differences between the respective sensor signals by performing a multilateration procedure based on phase differences between the respective sensor signals or by performing a trilateration procedure based on magnitude differences between the respective sensor signals, determining a magnitude attenuation factor based on the determined position of the living-being and a position of one of the sensors, and determining the biophysical variable based on a sensor signal generated by the one of the sensors and the magnitude attenuation factor.

The effect of the invention is that the sleep monitoring device uses only a few sensors to measure a biophysical variable of the living-being, such that the measured biophysical variable is robust for the position of the living-being relative to the sensors. An additional benefit is that the invention produces a useful intermediate parameter for sleep monitoring, namely the position of the living-being.

It will be appreciated by those skilled in the art that two or more of the above-mentioned options, implementations, and/or aspects of the invention may be combined in any way deemed useful.

Modifications and variations of the mobile device, the method, and/or of the computer program product, which correspond to the described modifications and variations of the mobile device, can be carried out by a person skilled in the art on the basis of the present description.

BRIEF DESCRIPTION OF THE DRAWINGS

These and other aspects of the invention are apparent from and will be elucidated with reference to the embodiments described hereinafter.

In the drawings.

It should be noted that items that have the same reference numbers in different figures, have the same structural features and the same functions. Where the function and/or structure of such an item have been explained, there is no necessity for repeated explanation thereof in the detailed description.

DETAILED DESCRIPTION OF EMBODIMENTS

Figure 1A:
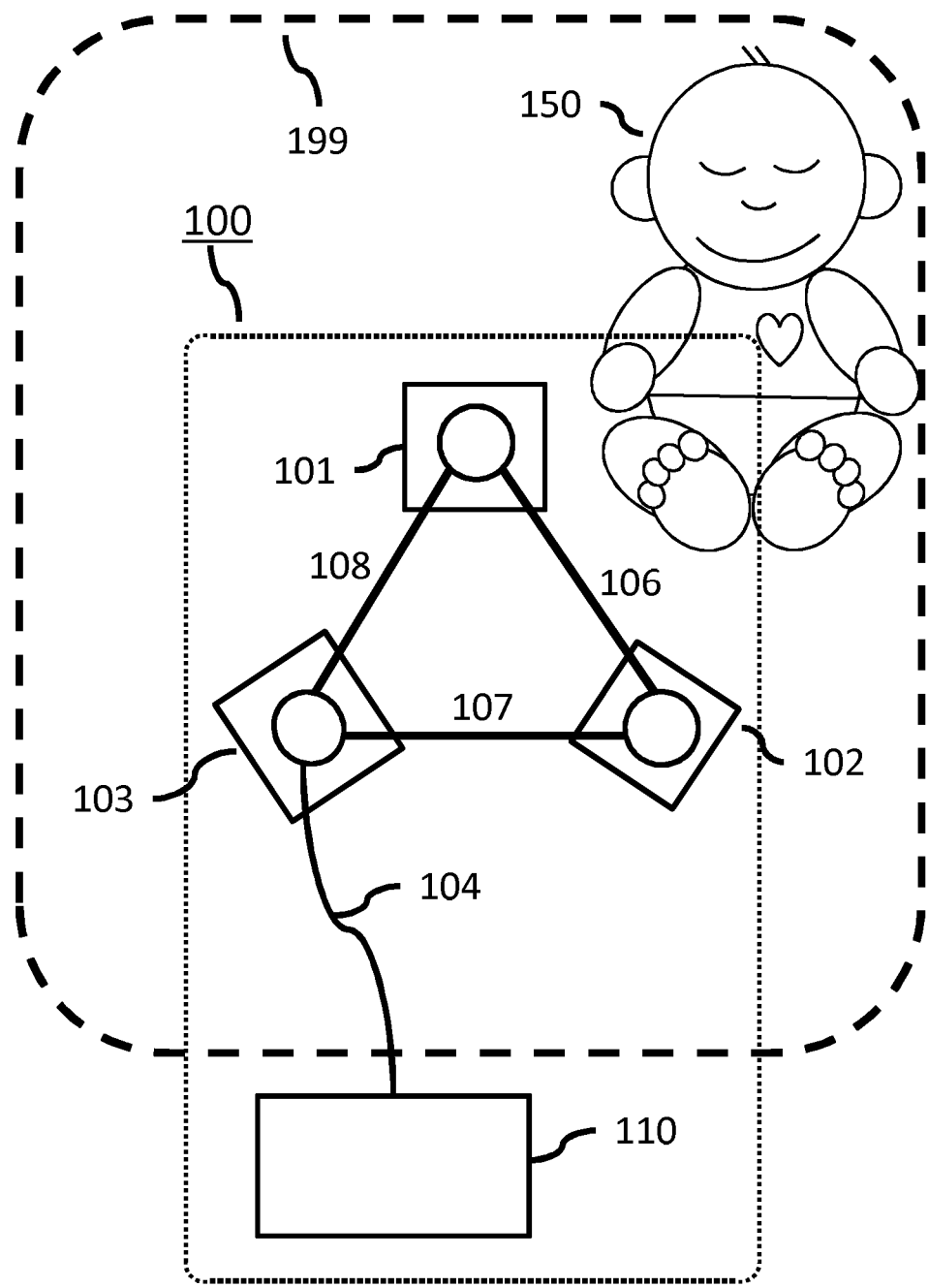
FIG. 1a illustrates the sleep monitoring device as a block scheme.

FIG. 1a illustrates the sleep monitoring device 100 used in a mattress 199 supporting an infant 150. The mattress 199 acts as a supporting layer that supports the lying infant. The device 100 comprises three (pressure) sensors 101-103 that generate respective sensor signals in response to pressure caused by the infant 150 via the mattress: a sensor signal at a sensor thus represents the pressure at the that sensor. The pressure may be caused by biophysical actions of the infant, such as breathing, ballistic movements of the heart and body movements. The sensors are spatially configured in a planar geometry so that the three sensors fit inside the mattress or directly under the mattress. The connectors 106-108 between the three sensors are sufficiently rigid to maintain the planar geometry in its pre-defined configuration.

The sleep monitoring device 100 comprises a processing unit 110 that receives the sensor signals from the sensors 101-103 via the cable 104 and via (along) cables running via the connectors 106-108. The processing unit 100 extracts a biophysical variable from the sensor signals that characterize a biophysical actions of the infant. For example, the biophysical variable is breathing rate and/or breathing intensity characterizing a breathing condition. Or the biophysical variable is heart rate and/or heart beat intensity characterizing a heart condition. Or the biophysical variable is an amount of body movements that may characterize a sleep state, e.g. much, prolonged body movement characterizing physical unrest or small, brief body moments characterizing a light sleep state.

The invention uses (at least) two sensors in order to measure a biophysical variable such that it has a correct magnitude, based on the following notion. The magnitude of the pressure at a sensor results from two causes: (1) the magnitude of the biophysical action and (2) the distance between the sensor and the infant. The distance thus causes an attenuation to the pressure caused by the biophysical action. In order to obtain the magnitude of the biophysical action, the sensor signal needs to be corrected for the attenuation caused by said distance. However, such a correction is not possible using a single sensor, because said distance is unknown and cannot be derived from the signal generated by the single sensor. The invention therefore employs a computational procedure that uses differences between sensor signals from respective sensors to estimate said distance and to correct the magnitude of the sensor signal based on the estimated distance. Below two computational procedures are explained further: multilateration based on phase/time differences and trilateration based on magnitude differences.

Note that the term attenuation in the current context relates to a decrease of the magnitude of the pressure or pressure wave as a result of propagating over a distance through the mattress (supporting layer). Also note that, in the current context, magnitude of the biophysical signal refers to the same matter as amplitude of the biophysical signal. A magnitude of the biophysical variable may (depending on the type of biophysical variable) also directly relate to the magnitude of the biophysical signal, for example when the biophysical variable is breathing intensity computed as the average magnitude of the biophysical during a 30-second period. In contrast, a magnitude of breathing rate/frequency is not related to the amplitude of the breathing signal.

Consider the following example case of the previous paragraph. The infant's breathing action generates a pressure wave causing the sensors 101-103 to generate respective sensor signals. Because the magnitude of the pressure wave attenuates as the pressure propagates though the mattress, a sensor near the infant (e.g. sensor 101) senses a larger pressure than a sensor far from the infant (e.g. sensor 103). The magnitude of the near sensor's signal is therefore larger than the magnitude of the far sensor's signal. As a consequence, a sensor signal with a given magnitude may correspond to different breathing conditions, e.g. the following two cases: (1) a heavily breathing baby (large pressure wave magnitude) from the infant being far from the sensor and (2) a normal breathing baby (smaller pressure wave magnitude) from the infant being near the sensor. From merely one sensor signal, one cannot dissociate these breathing conditions.

Figure 1B:
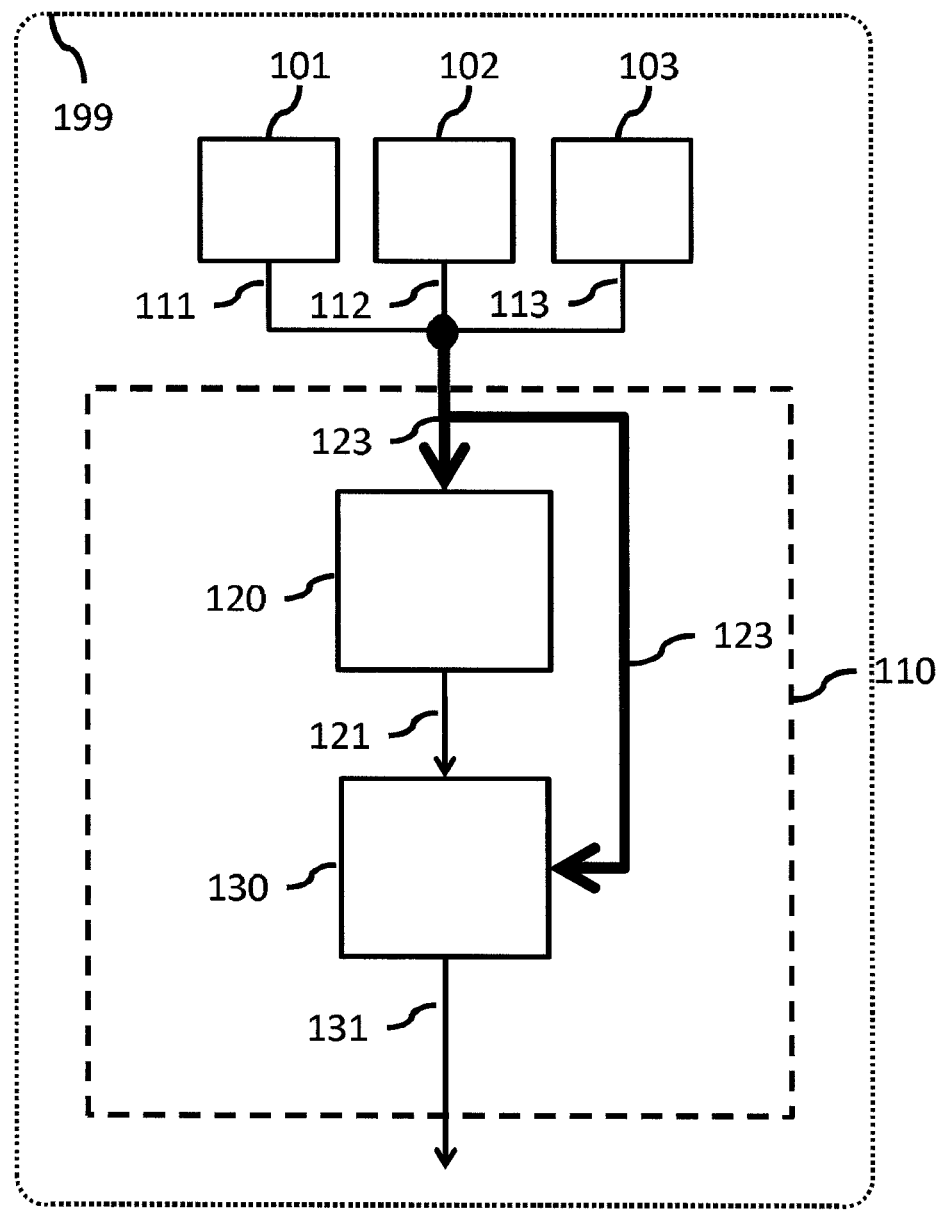
FIG. 1b illustrates the sleep monitoring device used in a mattress supporting an infant.

FIG. 1b illustrates the sleep monitoring device 100 as a block scheme. The sleep monitoring device 100 comprises the three sensors 101-103 that generate respective sensor signals in response to pressure caused by the infant. The sensor signals are fed to the processing unit 110 via respective cables 111-113 joining into a cable 123. The processing unit 110 then obtains the biophysical variable 131 from the sensor signals.

The processing unit 110 comprises a localization function 120 and a determining function 130. In short, the localization function 120 determines the infant's position 121 from differences between the sensor signals, whereas the determining function 130 determines the biophysical variable 131, taking the determined position 121 of the infant 150 into account to compute the magnitude of the biophysical variable 131.

Figure 2:
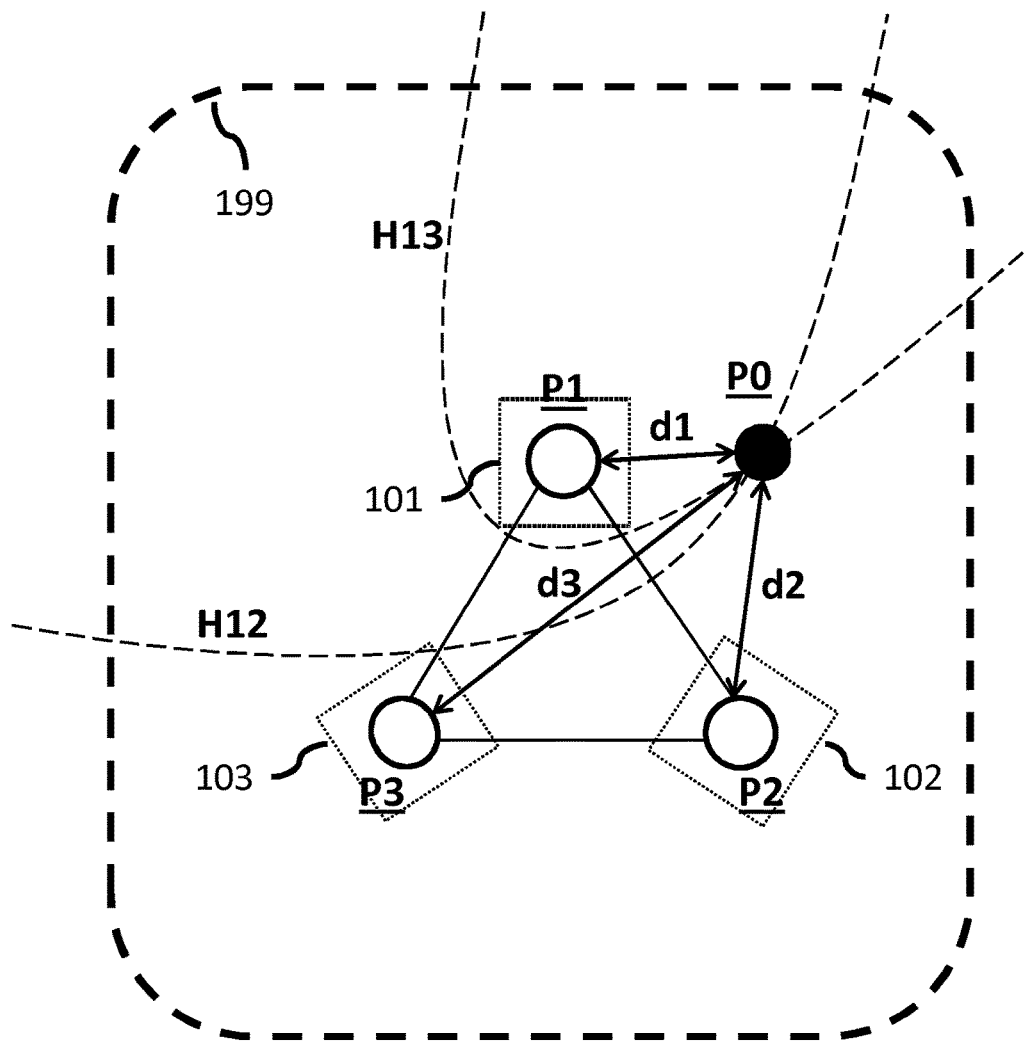
FIG. 2 illustrates a multilateration procedure for locating the infant on the mattress.

FIG. 2 illustrates a multilateration procedure for locating the infant 150 on the mattress 199. Such a process is employed by the localization function 120. The situation as depicted in FIG. 2 corresponds to FIG. 1a, showing three sensors 101-103 in a mattress 199. Position P0 corresponds to the position of the infant 150 on the mattress 199, whereas positions P1, P2 and P3 correspond to the sensors 101, 102 and 103, respectively. The infant 150 acts as a source of pressure waves causing the sensors 101-103 to respond by generating respective sensor signals.

The pressure waves thus propagate from the source at position P0 across sensor-source distances d1, d2 and d3 to the respective sensors 101, 102 and 103 at the respective positions P1, P2 and P3. Propagation properties of pressure waves depend on material properties of the mattress 199. The propagation properties include: (1) a propagation speed and (2) an attenuation function that describes attenuation of the pressure wave magnitude as a function of (propagation) distance. As the sensor positions P1-P3 differ, the sensor-source distances d1-d3 differ and, consequently, a pressure wave from the source results in pressure waves at the sensors 101-103 that differ in magnitude and timing (delay). The resulting sensor signals therefore differ in magnitude and delay. For example, when sensors 101 and 103 generate respective sensor signals in response to a pressure wave from the source, then the sensor signal from sensor 103 will have a larger delay and smaller magnitude as compared to the sensor signal from sensor 101.

The multilateration procedure serves to compute the position of the source from the three sensor signals. The multilateration procedure is based on timing differences between the three sensor signals (also commonly known as time differences of arrival, or TDOA). The sensor signal from sensor 102 is delayed with respect to the sensor signal from sensor 101, say by an amount DELAY12. Hyperbola H12 represents all possible source positions that correspond to the delay DELAY12. (In other words, hyperbola H12 represents all source positions from where the source would generate the same delay DELAY12 between the sensors 101 and 102.) Likewise, the sensor signal from sensor 103 is delayed with respect to the sensor signal from sensor 101, say by an amount DELAY13. Hyperbola H13 then represents all possible source positions that correspond to the delay DELAY13. The source position P0 is thus derived from the sensor signals by calculating the intersection of the two hyperbolas H12 and H13. (A skilled person is considered to be capable to compute the intersection of two hyperbolas using textbook calculus).

A delay between two signals (e.g. sensor signals) may be computed by means of a cross-correlation between the two signals. The time at which the cross-correlations exhibits a peak indicates the delay. Alternatively, signal processing may be applied to compute the onset the two signals after a period of silence. The time difference between the onsets then indicates the delay.

Multilateration may further be based on a third delay, say delay DELAY23, between the sensor signals of the sensors 102 and 103. The delay DELAY23 would correspond to a third hyperbola H23 (not shown) representing possible source positions. The source position is then derived by calculating the intersection of the three hyperbolas. Ideally, the three hyperbolas intersect at exactly the same position P0. Yet, in practice the three hyperbolas intersect at the approximately the same position, due to signal noise other practical inaccuracies in the procedure. The final source position may then be derived by first (a) calculating the (three) intersections of the respective three pairs of hyperbolas and then (b) calculating an average position from the three intersections.

Figure 3A:
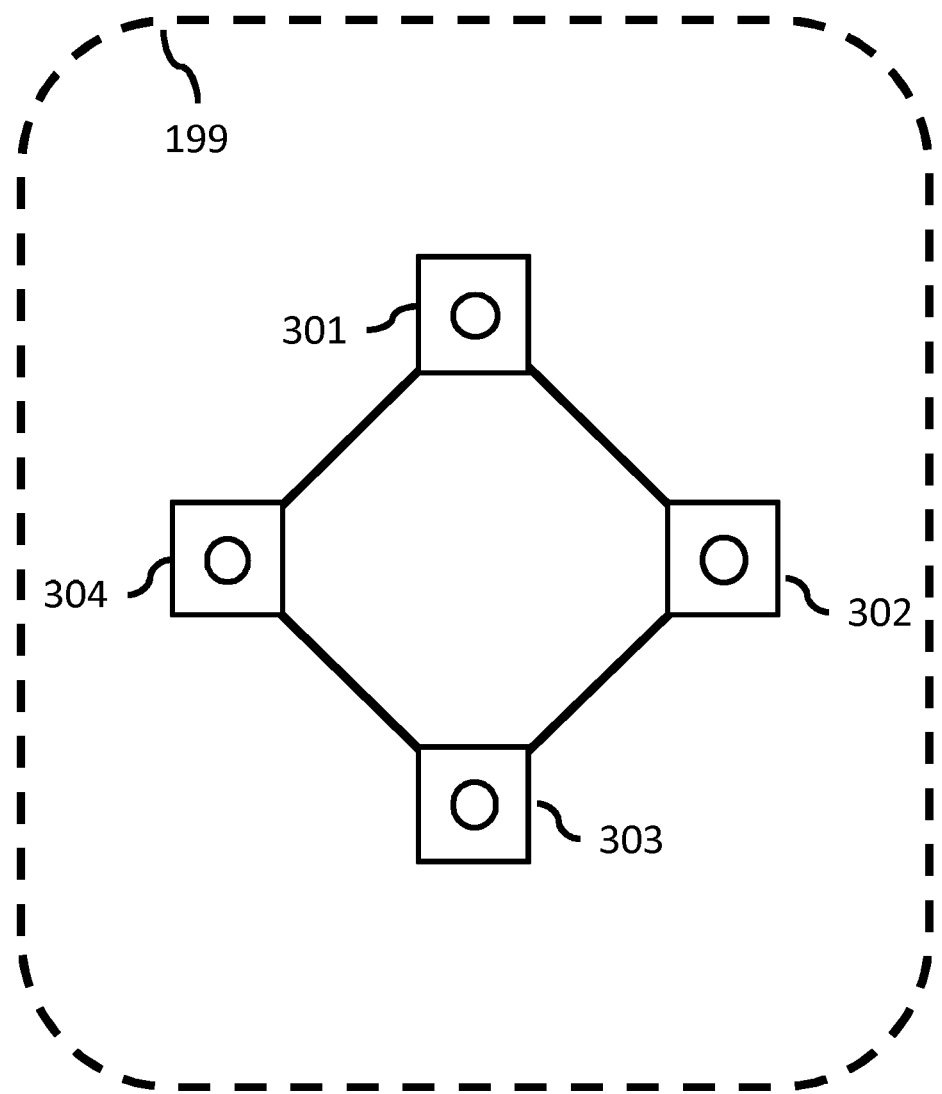
FIG. 3a illustrates a sleep monitoring device using four sensors.
Figure 3B:
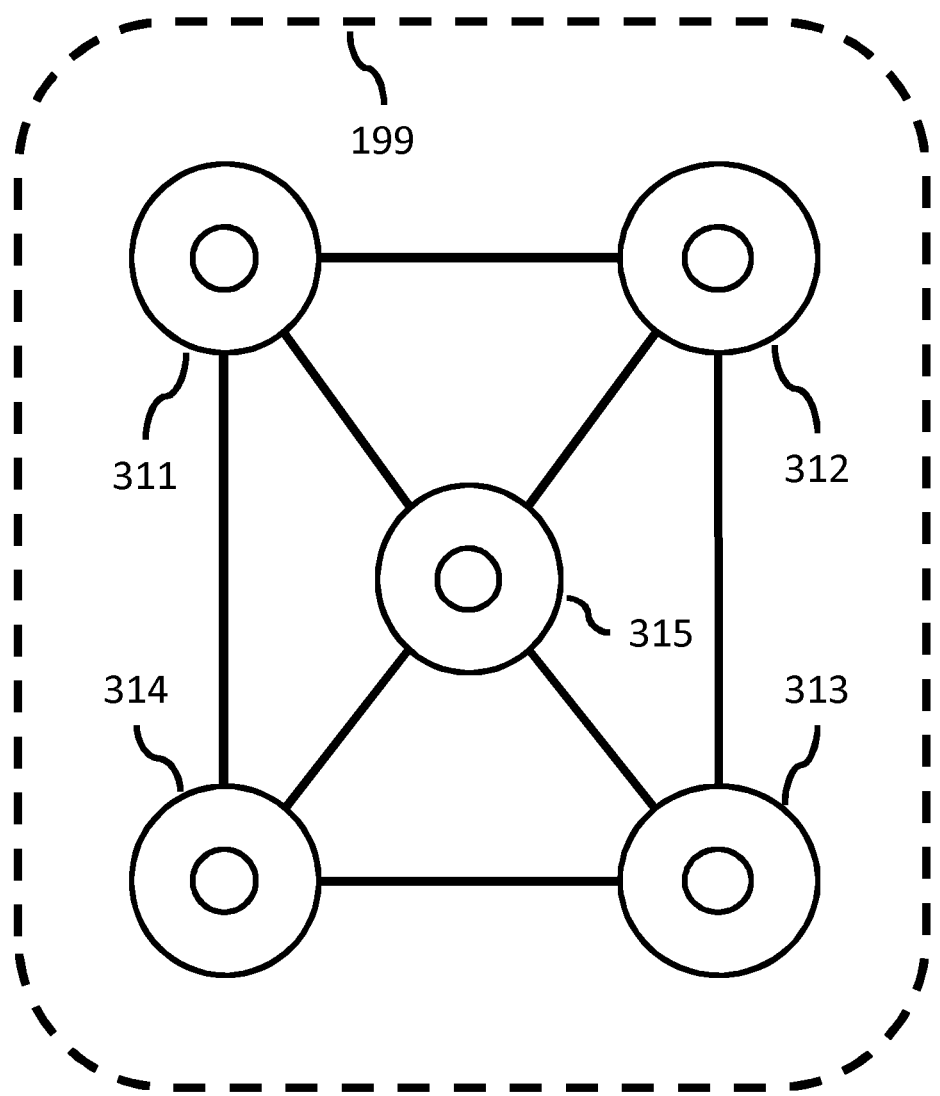
FIG. 3b illustrates a sleep monitoring device using five sensors.

Although a minimum of three sensors is required to perform the multilateration procedure, the multilateration procedure may also be performed with more than three sensors. FIG. 3a illustrates a sleep monitoring device using four sensors 301-304. The sensors are configured in a geometry having a diamond-like shape. Any other quadrilateral shape is also possible, for example a diamond-like shape. FIG. 3b illustrates a sleep monitoring device using five sensors 311-315. The fifth sensor 315 is at the center of a rectangular geometry formed by the first four sensors 311-314. Other configurations having more than five sensors in a planar geometry and in any possible configuration may also be used. The shapes and sizes as shown in FIGS. 3a and 3b are chosen such that the sensors are distributed fairly uniformly over the mattress. In this way, it is likely that at least one of the sensors is near the infant 150, so that that sensor measures signals from nearby the infant and provides a sensor signal with a relatively high signal-to-noise ratio (as compared to a sensor farther way). Furthermore, spacing the sensors sufficiently apart creates sufficiently large differences between the sensor signals, which is beneficial for the accuracy of a procedure (such as the multilateration procedure) that computes a source position from these differences. If the sensors are spaced closer together, the accuracy of the computed source position tends to deteriorate.

Determining the source position for more than three sensors is done in an analogous way as described in the previous paragraph. From N sensors, ½N×(N−1) unique sensor pairs can be formed, each pair corresponding to a hyperbola. Thus, 3 sensor pairs can be formed from 3 sensors, 6 sensor pairs from 4 sensors, 10 sensor pairs from 5 sensors, etcetera. A hyperbola can be determined for each pair of sensors, and an intersection can be determined for each pair of hyperbolas. The final source position may be derived by calculating the average of the determined intersections of respective pairs of hyperbolas.

The infant 150 may be localized based on magnitude differences between sensor signals rather than timing differences between sensor signals. The offset of a sensor signal depends on the static pressure exerted by the infant 150. Without an infant on the mattress 199, the sensor signal has a base offset. With the infant 150 on the mattress, the sensor signal has an other offset. The difference between the other offset and the base offset is thus caused by static pressure exerted by the infant. The exerted static pressure depends on both (a) the infant's weight and (b) on the position P0 of the infant 150 relative to the sensors, but the contribution of the infant's weight to the exerted static pressure may be cancelled out, and that the offset difference in the sensor signal can then be related to the position P0 of the infant.

Figure 4:
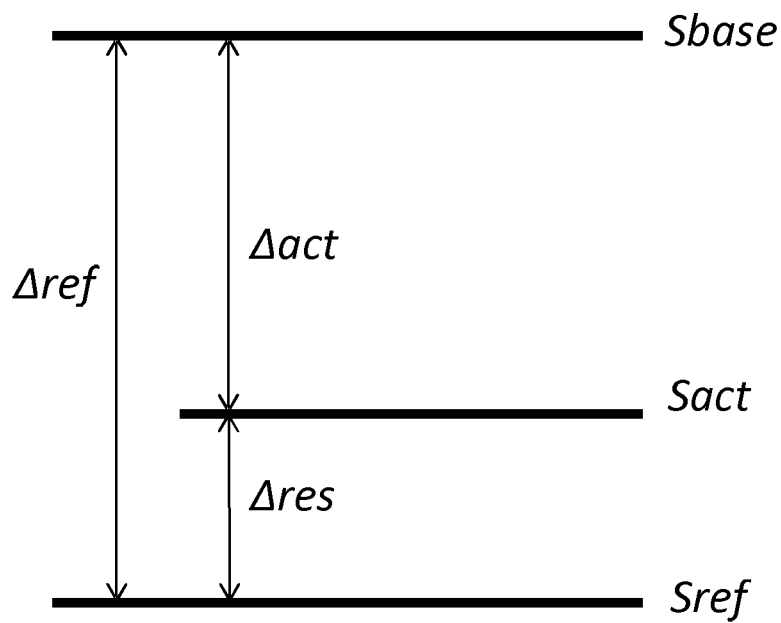
FIG. 4 illustrates offsets of the sensor signal in respective different situations.

FIG. 4 illustrates offsets of the sensor signal in respective different situations. Cancelling out the contribution of the infant's weight in the offset difference is done by calibrating the sensor signal of a sensor, e.g. sensor 101. First, the base offset Sbase of the sensor signal is measured when the infant is not on the mattress. Second, a reference offset Sref is measured when the infant is on the mattress, directly above the sensor. Then, a reference offset difference Δref is computed as the (absolute) difference Δref=|Sref−Sbase|, i.e. between the reference offset and the base offset. When the infant is not directly above the sensor (e.g. the infant is at position P0) an actual offset Sact of the sensor signal is measured. An actual offset difference Δact is then computed as Δact=|Sact−Sbase|, i.e. the (absolute) difference between actual offset and reference offset. The actual offset difference Δact is smaller than the Δref, because the pressure exerted on the sensor becomes smaller as the infant moves away from the sensor. A 'residual' offset difference, being Δres=Δref−Δact, therefore results from the difference d1 between the position P1 of sensor 101 and position P0 of the infant. By computing the residual offset difference Δres the contribution of the infant's weight Δact to the reference offset difference Δref is effectively cancelled out.

The residual offset difference Δres may be related to a source-sensor distance, e.g. the sensor-source distance d1 between the sensor 101 and the source position P0. The sensor-source distance may be determined using an attenuation function (i.e. similar to attenuation curve 650 shown in FIG. 6b) that describes how the residual offset difference Δres relates to the source-sensor distance. The attenuation function may be obtained through another calibration procedure wherein (1) an object of the same size and weight as the infant is placed on various distances to the sensor, (2) an offset of the sensor signal is measured at each of the various distances, and (3) the residual offset difference Δres is computed for each of the measured offsets.

By measuring respective residual offset differences Δres for multiple sensors (e.g. for each of sensors 101-103) a sensor-source distance (e.g. d1-d3) may be determined for each of the multiple sensors. The infant may be localized using a trilateration procedure based on the multiple sensor source distances d1-d3.

Alternatively, magnitude differences between sensor signals are not derived from using offset, such as described above, but from amplitude of the dynamic component of each sensor signal. In a calibration procedure, a simulator (a dummy infant) causing similar pressure waves as an infant may be placed at various positions on the supporting layer. Through such a calibration procedure, the attenuation of the magnitude of a biophysical signal (for example, a breathing signal, heart signal or body moment) as a function of position of the simulator relative to the position of a sensor may be determined. Thus, both the static component (offset) of the sensor signal as well as the dynamic component (amplitude) may be used to determine the location of the infant based on differences in magnitude between the sensor signals.

Figure 5A:
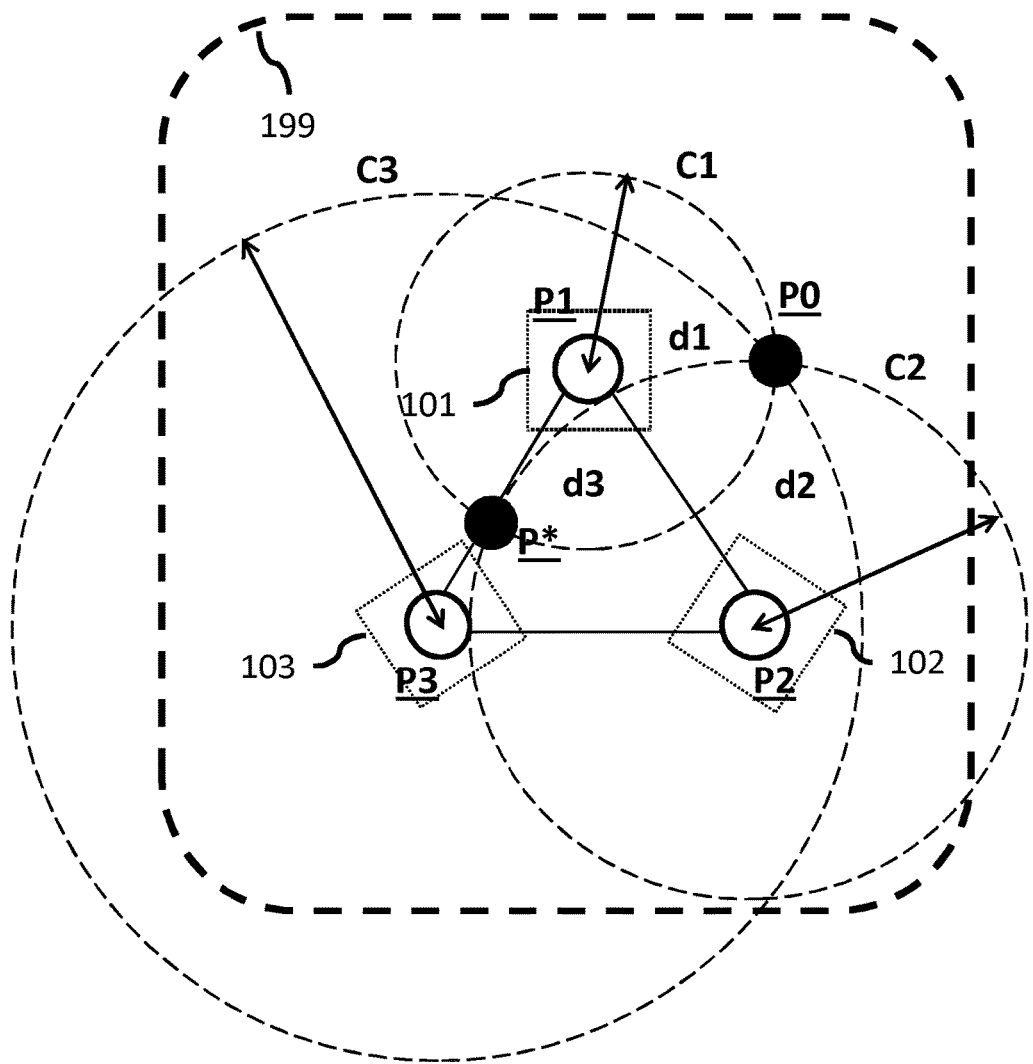
FIG. 5a illustrates a trilateration procedure for locating the infant on the mattress.

FIG. 5a illustrates a trilateration procedure for locating the infant 150 on the mattress 199. Such a process is employed by the localization function 120. The situation as depicted in FIG. 5a is similar to FIG. 2, but differs in the sense that a sensor-source distance d1-d3 is directly obtained from the (single) respective sensor signal only (as described above). Source positions that lie at a distance d1 re. the sensor 101 are indicated by circle C1. Likewise, source positions at distance d2 re. sensor 102 are at circle C2, and source location at distance d3 re. sensor 130 are at circle C3. The infant 150 is localized at location P0 by determining the intersection of circle C1, C2 and C3 using textbook calculus.

In FIG. 5a, all three circles C1-C3 are required to determine location P0 uniquely. If only two circles were used, a unique location cannot be determined. For example, circles C1 and C2 intersect at two locations, P0 and P*. In this example, the third circle C3 is thus needed to determine the location P0 as the unique intersection of the three circles C1-C3.

Figure 5B:
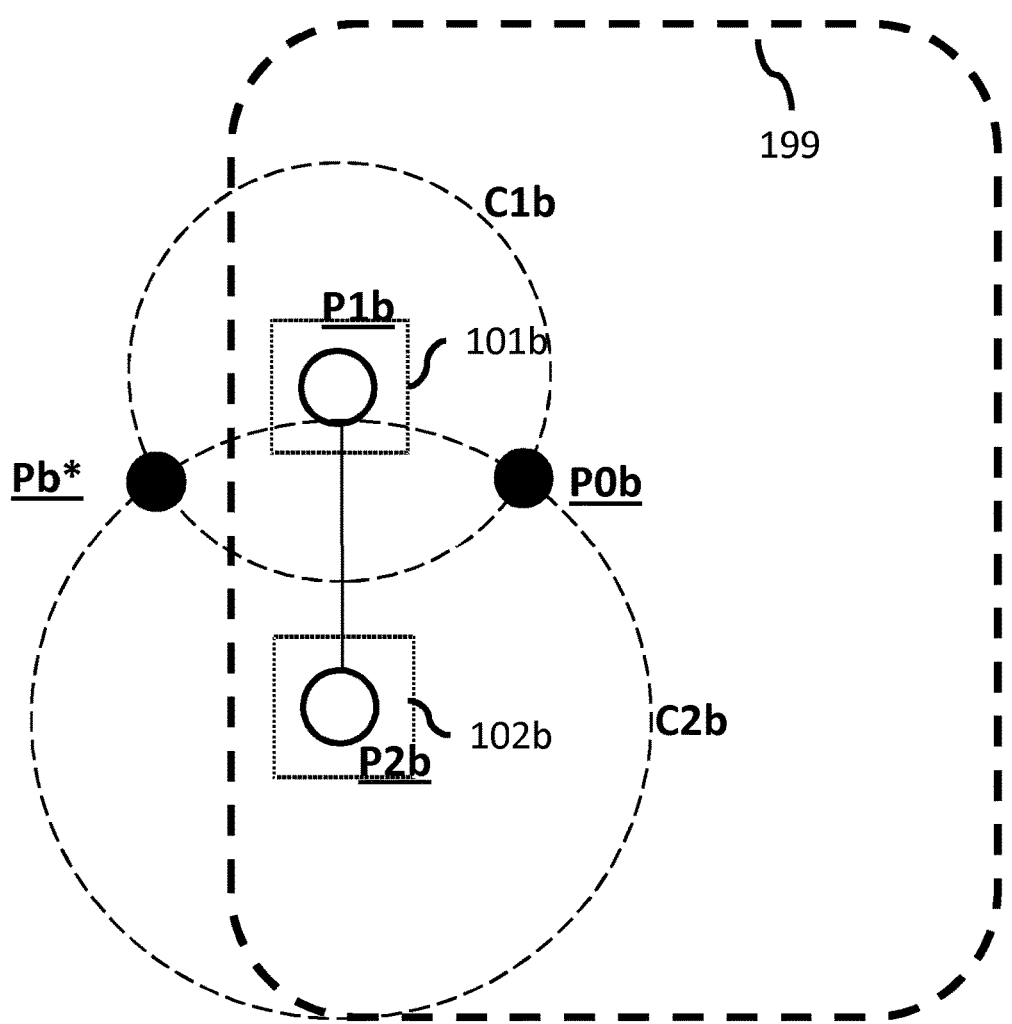
FIG. 5b illustrates a trilateration procedure using only two sensors.

FIG. 5b illustrates a trilateration procedure using only two sensors 101b and 102b. FIG. 5b shows an example, wherein the sensors 101b and 102b are placed at an edge of the mattress 199, at respective positions P1 and P2. Note that FIG. 5b is similar to FIG. 5a, but that two sensors 101b and 102b are placed at the edge and that the third sensor 103 is absent. In this example, only the two sensors 101b and 102b are needed to determine a unique intersection P0. As the second intersection at location P* lies outside the mattress, location P* may therefore be excluded as a possible location of the infant. Note that localizing the infant 150 using only two sensors is done on the basis of magnitude differences between the sensor signals of sensors 101b and 102b.

Figure 6A:
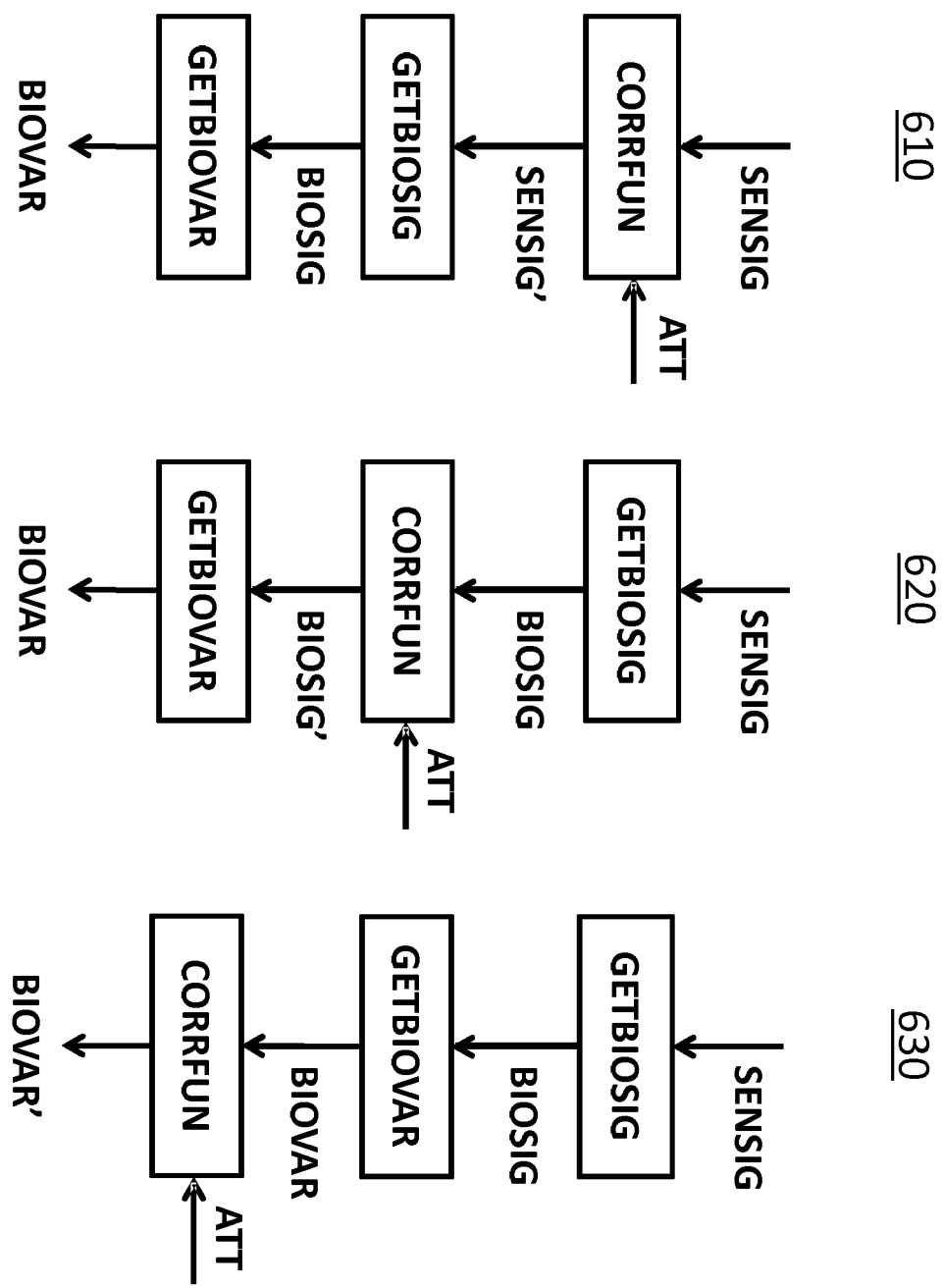
FIG. 6a illustrates three processes for determining a biological variable from the sensor signal.

FIG. 6a illustrates three processes for determining a biophysical variable BIOVAR from the sensor signal SENSIG. A process such as illustrated by block schemes 610-630 is employed by the determining function 130. Each block in FIG. 6a represents a subfunction.

According to process 610, the determining function 130 works as follows. Subfunction CORRFUN corrects the magnitude of a sensor signal SENSIG using an attenuation parameter ATT and produces a corrected sensor signal SENSIG'. Subfunction GETBIOSIG filters the biophysical signal BIOSIG from the corrected sensor signal SENSIG'. Subfunction GETBIOVAR extracts the biophysical variable BIOVAR form the biophysical signal BIOSIG. For example, the biophysical signal BIOSIG is a breathing signal, a heart signal, or a body movement signal, and the biophysical variable is breathing intensity, heart beat intensity or body movement intensity, respectively.

Note that the terminology 'signal B is filtered from signal A' implies that a filter is applied to signal A, resulting in signal B. For example, the filter is a bandpass filter.

Process 620 differs from process 610 in that the order of subfunctions CORRFUN and GETBIOSIG is swapped in process 620 compared to process 610. Thus, the magnitude of the biophysical signal is corrected, rather than the magnitude of the sensor signal. According to process 620, the determining function 130 then works as follows. Subfunction GETBIOSIG filters the biophysical signal BIOSIG from the sensor signal SENSIG. Subfunction CORRFUN corrects the magnitude of the biophysical signal BIOSIG using an attenuation parameter ATT and produces a corrected biophysical signal BIOSIG'. Subfunction GETBIOVAR extracts the biophysical variable BIOVAR from the corrected biophysical signal BIOSIG'.

Process 630 is a third variant for determining a biophysical variable BIOVAR' from the sensor signal SENSIG. In this variant, the subfunction CORRFUN is applied to the biophysical variable BIOVAR that is extracted from the biophysical signal BIOSIG. Subfunction CORRFUN corrects the magnitude of a biophysical variable BIOVAR using an attenuation parameter ATT and produces a corrected biophysical variable BIOVAR'.

As an example of subfunction GETBIOSIG, consider a breathing signal being filtered from the (either corrected or not) sensor signal using a band-pass filter having a pass band of, for example, 0.1-2 breathing cycles/second (Hz). The low end of the pass band serves to exclude a DC component at 0 Hz. The high end of the pass band serves to include the highest frequencies of the breathing signal. An infant's breathing rate, being typically about 0.5-1 breathing cycles/second, falls within the pass band. The breathing signal is obtained by applying the band-pass filter to the corrected sensor signal.

As another example of subfunction GETBIOSIG, a heart signal is filtered from the (either corrected or not) sensor signal in a similar manner, albeit in a high frequency range, for example 1-250 Hz. The heart signal is caused by ballistic movements of the heart that generate pressure waves, and the resulting heart signal is commonly referred to as the ballisto-cardiogram.

As an example of subfunction GETBIOVAR, a biophysical variable being breathing rate or breathing intensity is extracted from the (either corrected or not) breathing signal. For example, the breathing rate is extracted by applying signal processing to determine the average base frequency of the breathing signal during a predetermined (e.g. 30-sec) period. Similarly, the breathing intensity is extracted by applying common signal processing to determine the average amplitude of the breathing signal during said predetermined period.

As another example of subfunction GETBIOVAR, the biophysical variable being heart rate or heart beat intensity is extracted from the (either corrected or not) heart signal. For example, the heart rate is extracted by applying signal processing to determine the average base frequency of the heart signal during a predetermined (e.g. 30-second) period. Similarly, the heart beat intensity is extracted by applying common signal processing to determine the average amplitude of the heart signal during such a predetermined period.

As an example of subfunction CORRFUN, an attenuation parameter ATT being a number between 0.0 and 1.0 expressing the extent to which the magnitude (amplitude) by which the sensor signal SENSIG (or the biophysical signal BIOSIG) is attenuated as result of propagating over the distance between the signal source and the sensor that generates the sensor signal SENSIG. For example, the number 0.8 expresses that the magnitude of the sensor signal (or biophysical signal BIOSIG) at the sensor is 80% of the magnitude of the sensor signal at the source location P0. In other words, the sensor signal lost 20% of its magnitude as a result of propagating from the source to the sensor. When applied in process 610, the subfunction CORRFUN then obtains the corrected sensor signal SENSIG' by multiplying the sensor signal SENSIG by 1/0.8. When applied in process 620, subfunction CORRFUN obtains the corrected biophysical signal BIOSIG' by multiplying the biophysical signal BIOSIG by 1/0.8. When applied in process 630, subfunction CORRFUN obtains the corrected biophysical variable BIOVAR' by multiplying the biophysical variable BIOVAR by 1/0.8. (Note that the corrections in the example above by subfunction CORRFUN are done under the assumption that all frequencies of pressure waves propagate in the same manner through the mattress.)

Figure 6B:
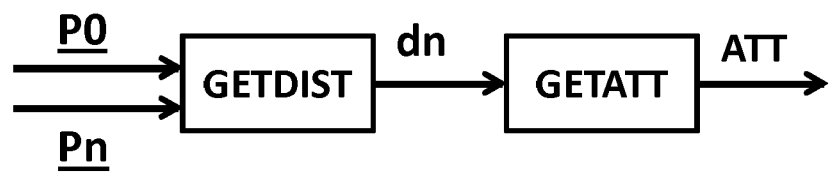
FIG. 6b illustrates an auxiliary process that determines the attenuation parameter used in the three processes.
Figure 6B:
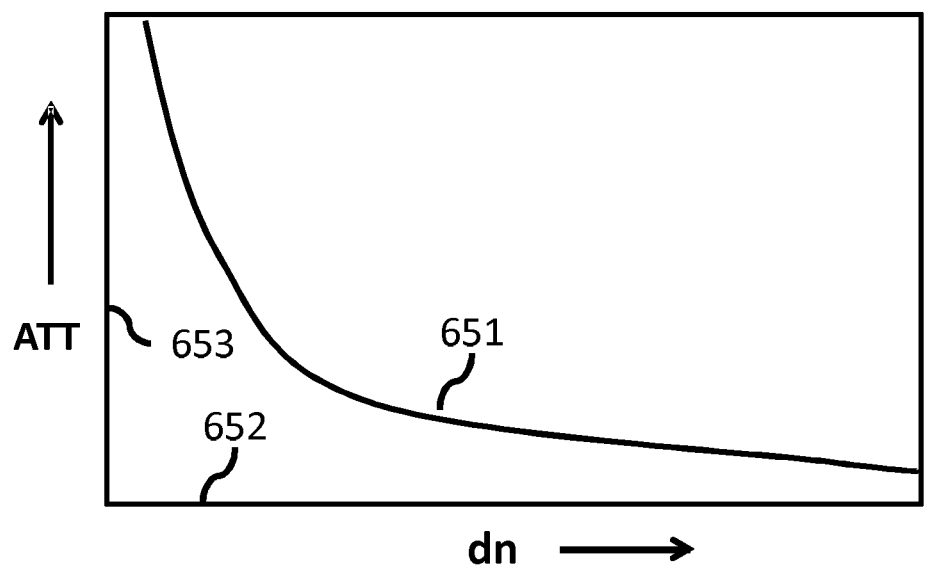

FIG. 6b illustrates auxiliary process 640 that determines the attenuation parameter ATT for in the three processes 610-630. Subfunction GETDIST computes the source-sensor distance dn between the source position (provided/determined by the localization function 120) and the (known) sensor position Pn. For example, the sensor 101 generates the sensor signal SENSIG, the sensor position Pn=P1 and the distance dn=d1 (see also FIG. 2). Subfunction GETATT then determines the attenuation parameter ATT by using an attenuation curve that relates source-sensor distance dn to a magnitude attenuation factor ATT.

For example, graph 650 shows an attenuation curve 651 having source-sensor distance dn on the x-axis 652 and attenuation parameter ATT (i.e. being a magnitude attenuation factor in this example) on the y-axis 653. Attenuation curve 651 describes that the magnitude of sensor/biophysical signal becomes gradually smaller as the source-sensor distance dn becomes larger. Subfunction GETATT thus relates the computed source-sensor distance dn to the attenuation parameter ATT via the attenuation curve 651.

The attenuation curve 651 may be defined by as the attenuation parameter ATT being inversely proportional to the sensor-source distance dn. For example, $ATT=dn_0/dn$, for $dn>dn_0$, and $ATT=1$ for $dn \leq dn_0$, wherein $dn_0$ represents a minimum distance to the source (e.g. $dn_0=15$ cm). Alternatively, the attenuation curve 651 may be inversely proportional to a power K of the inverse of the sensor-source distance dn: $ATT=(dn_0/dn)^K$, for $dn>dn_0$, and $ATT=1$ for $dn \leq dn_0$, e.g. $K=2$.

Ultimately, the attenuation curve 651 is determined by the propagation properties of the mattress. In the case that attenuation can be described according to the latter equation, a calibration procedure may be used to determine parameters K and $dn_0$. For example, the calibration procedure uses a device that generates vibrations (having frequencies in the range of biophysical signals of interest) and the attenuation curve 651 is sampled (measured) at various sensor-source distances dn. A least-squared error fit then yields the parameters K and $dn_0$. Or, if one of the two parameters K and $dn_0$ is already known, the least-squared error fit yields the other, unknown parameter.

Propagation properties may differ for different frequencies of pressure waves through the mattress. For example, an attenuation curve 651 may need to be determined for each frequency band. For example, a first frequency band includes the breathing signal and a second frequency band includes the heart signal each: the first frequency band then corresponds to a first attenuation curve 651 and the second frequency band then corresponds to a second (different)

attenuation curve 651. In process 620, subfunction COR-RFUN then corrects the magnitude of the biophysical signal BIOSIG using an attenuation parameter ATT corresponding to the frequency band of the biophysical signal BIOSIG. Likewise, process 630, subfunction CORRFUN then corrects the magnitude of the biophysical variable BIOVAR using an attenuation parameter ATT corresponding to the frequency band of the biophysical signal BIOSIG.

Differences in propagation properties may include different propagation speeds within respective different frequency bands. A breathing signal and a heart rate signal may therefore each propagate with its own propagation speed. The multilateration procedure may then be performed on the basis of the breathing signal or the heart signal, rather than on the sensor signal. In FIG. 2, this may work as follows. Sensor signals from the respective three sensors 101-103 are filtered such that respective three breathing signals are obtained from the sensor signals. The multilateration procedure is then performed on the basis of the three breathing signals and a propagation speed of the breathing signals in the mattress. In an analogous manner, the multilateration procedure is performed on the basis of the heart signal.

The determining function 130 may select the sensor signal having the largest magnitude from the available sensor signals to determine the biophysical variable. For example, consider FIG. 2. If the sensor signal generated by sensor 101 has a larger magnitude (amplitude) than the sensor signals, i.e. generated by sensors 102 and 103, then the determining function 130 selects the sensor signal from sensor 101. The biophysical variable is determined from the selected sensor signal, according to one of the processes 610-630.

In an analogous manner, the determining function 130 may select the biophysical signal (rather than the sensor signal) having the largest magnitude from the available biophysical signals. To that end, the determining function 130 filters a breathing signal from each of the sensor signals and selects the breathing signal having the largest magnitude. The biophysical variable may then be determined from the selected breathing signal, e.g. according to process 620.

Alternatively, the determining function 130 may determine the biophysical variable from multiple sensor signals (i.e. generated by respective multiple sensors) rather than from a single sensor signal. Consider the following example consistent with process 610. The multiple sensor signals from respective multiple sensors (e.g. 101-103) are shifted along the time axis to align the respective phases of the multiple sensor signals. The magnitude of each of the time-shifted sensor signals is then corrected using subfunction CORRFUN. A 'super sensor signal' is then obtained by computing an average of the (magnitude-) corrected time-shifted sensor signals, a biophysical signal is filtered from the super sensor signal, and the biophysical variable is extracted from the biophysical signal.

Analogous to the previous paragraph, consider the following example consistent with process 620. Multiple biophysical signals are filtered from each of the respective multiple sensor signals from the respective multiple sensor signals. Similar to the previous paragraph, the multiple biophysical signals are time-shifted and magnitude-corrected, and a 'super biophysical signal' is obtained by computing an average of the magnitude-corrected time-shifted biophysical signals. The biophysical variable is then extracted from the super biophysical signal.

Alternatively, a biophysical variable is extracted from each sensor signal. The biophysical variables are then corrected according to process 630, and averaged into a 'super biophysical variable'.

Optionally, the average described in the previous three paragraphs may be a weighted average wherein the weights depend on (increase with) the magnitude of the corresponding sensor signal. A lower magnitude results in a low weight, and large magnitude results in a high weight. Assuming a constant noise level in the sensor signal, a weight then reflects a signal-to-noise ratio, and a contribution to the weighted average thus increases with the signal-to-noise ratio.

Body movement represents another biophysical variable of an infant. Body movements of an infant typically generate pressure waves that are much larger than pressure waves caused by ballistic movements of the heart or caused by the infant's breathing: the magnitude of a (raw) sensor signal is dominated by body movement. Body movement is therefore quantified in a straightforward manner by averaging the magnitude of a sensor signal in a predetermined time interval, for example a 30-second interval. Similar as other aforementioned biophysical signals, pressure waves caused by body movements are also attenuated as a consequence of propagating through the mattress.

Note that for determining the biophysical variable being body movement it is not necessary to compute an 'intermediate body movement signal'. Instead, body movement is thus directly extracted from the sensory signal. Or, in other words, the body movement signal equals the sensory signal (making the subfunction GETBIOSIG in FIG. 6*a* effectively an all-pass filter), and body movement is then extracted from the body movement signal.

Figure 7:
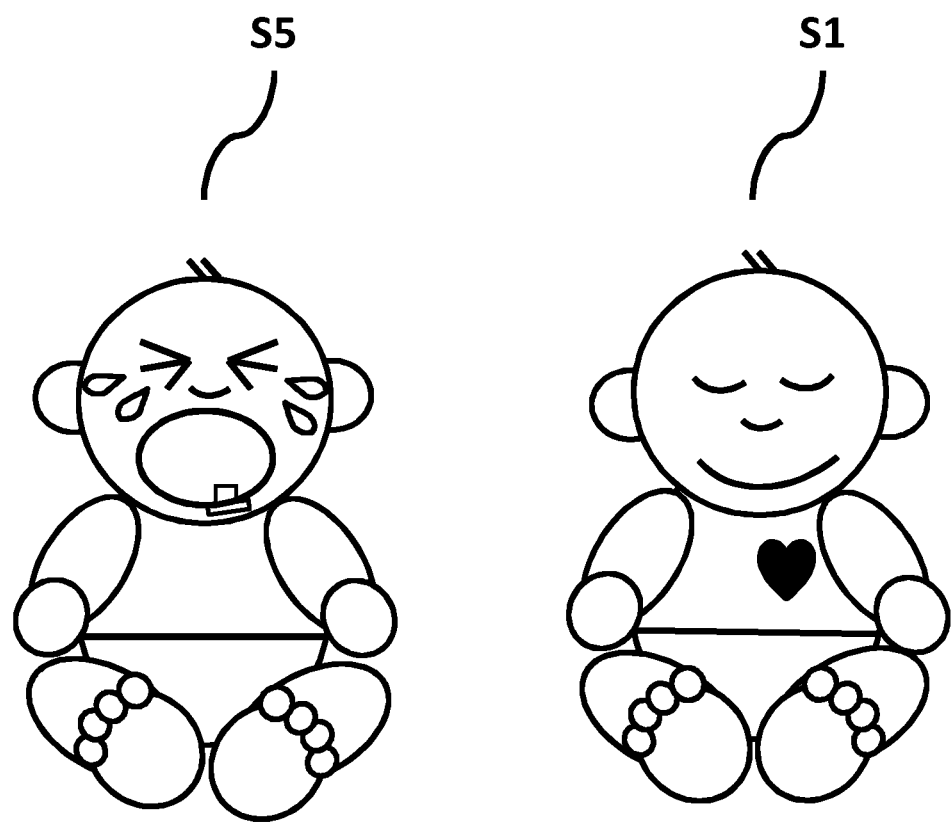
FIG. 7 illustrates two sleep states of an infant.

An infant's sleep state is characterized by various biophysical variables being in certain respective ranges. The various biophysical variables typically including heart rate, breathing rate (or 'respiration rate') and body movement. For example, in one sleep state the infant typically exhibits much body movement, a high heart rate and a high breathing rate, whereas in another sleep state the infant typically exhibits a low respiration rate, a moderate heart rate and little body movement. The various biophysical variables combined are thus an indicator for the sleep state of the infant. Five different sleep states are commonly distinguished for an infant: quiet sleep, active sleep, quiet alertness, active alertness, and vocalization. FIG. 7 illustrates two sleep states S1 and S5 of an infant. For example, sleep state S1 corresponds to quiet sleep, whereas sleep state S5 corresponds to vocalization.

For the purpose of monitoring sleep state, biophysical variables are typically measured in pre-determined intervals, for example 20- or 30-second intervals. For example, to determine heart beat intensity, an average magnitude of a (magnitude-corrected) heart signal is determined within the pre-determined interval; or to determine breathing intensity, an average magnitude of (magnitude-corrected) breathing signal is determined within the pre-determined interval; or to determine body movement, the average magnitude of a (magnitude-corrected) sensor signal is determined within the pre-determined interval.

The sleep monitoring device 100 may monitor the location the infant 150 by locating the infant 150 at regular intervals, for example once every minute or 30 seconds. The sleep determining device 100 may determine how much the infant's location changes during a sleep period. Much change of the infant's location may indicate restlessness. Little change of the infant's location may indicate that the infant is in a quiet state. Too little change of the infant's location during a long period may indicate that the infant is too quiet and may have a problem. Both a multilateration procedure (FIG. 2) and a trilateration procedure (FIG. 5) may be used to determine the infant's location.

Correcting for the attenuation of pressure waves (e.g. according to processes 610-630) bears particular relevance for biophysical variables that depend on the magnitude of a sensor signal or biophysical signal. For example, body movement is computed as the average magnitude (in a predetermined time interval) of a sensor signal. Therefore, if no magnitude correction is made to the sensor signal, then body movement is underestimated due to attenuation because of a distance between the sensor and the infant. Likewise, correcting magnitude of biophysical variables such as breathing intensity and heart-beat intensity prevents underestimation of these biophysical variables.

Although embodiments are described with an infant as the source of pressure waves, the embodiments need not be limited to infants but may also apply to adults or even animals. In short, any living-being capable of causing pressure waves through a mattress by means of, for example, breathing, heart beat or body movement may take the role of the source of the pressure waves.

Although a mattress is used as an embodiment of a supporting layer in the descriptions above, other types of supporting layers may also be used. For example, the supporting layer may be the lining of a chair. A chair is typically curved, in contrast to a mattress that is typically flat. The chair may support a human adult. The sensors may be placed directly under the lining of the chair, making contact to the lining. Alternatively, the sensors are placed inside the lining of the chair. As the chair is curved and the lining of the chair follows the curvature of the chair, the planar geometry comprising the sensors need to be curved in a similar way in order to also follow the curvature of the (lining of) the chair. Therefore, the planar geometry may be shaped as flat plane or a curved plane, whatever fits the supporting layer.

Like the multilateration procedure of FIG. 2, the trilateration procedure of FIG. 5 may also be used to determine the location P0 of the infant 150 and to use the determined position to correct a magnitude of a biophysical variable or a biophysical signal, for example to correct a magnitude of a heart signal as described in embodiments hereinabove. Note that the attenuation curve 651 for the heart signal may differ from the attenuation function for the residual offset difference. Due to propagation properties of the supporting layer, (mattress) frequencies typical for a heart signal may attenuate differently as a function of source-sensor distance than the offset of the sensor signal (i.e. the static pressure exerted by the infant).

A sensor may be manufactured as a piezo element wedged between two plates of PVC material for example (or other rigid or semi-rigid material). FIG. 3a illustrates sensors as piezo elements wedged between square shaped plates. FIG. 3b illustrates sensors as piezo elements wedged between circular shaped plates. On one hand, the surface of such a plate should not be too large as compared to the mattress, so as to measure pressure accurately in terms of location on the mattress. On the other hand, the surface of the plates should not be too small, so as to accumulate enough pressure to sense pressure waves with relatively small magnitudes (e.g. such as caused by ballistic heart movements).

The piezo element has a preferred direction in the sense that the piezo element responds most to pressure in the preferred direction and responds least to pressure in a direction orthogonal to the preferred direction. The piezo element is wedged in such a way between the two plates that the preferred direction is mainly orthogonal to the surfaces of the respective two plates between which the sensor is wedged. In other words, the preferred direction is aligned with the normal vector of the surface(s). The sensor comprising a piezo element wedged between two plates is thus most sensitive (i.e. responds with largest magnitude) to pressure in said preferred direction orthogonal to the surfaces of the two plates. The sensors illustrated above (e.g. FIG. 1 or FIG. 4a, 4b) have preferred direction that is orthogonal to a planar geometry in which the sensors are spatially arranged. The sensors and the planar geometry are oriented in the same direction.

A sensor may include an accelerometer that generates a sensor signal in response to pressure waves caused by the infant. An accelerometer may be particularly beneficial for sensing the relatively small signals caused by ballistic movements of the beating heart of the infant. A sensor may have one or more accelerometers in addition to or instead of a piezo element. The sleep monitoring device may have mixture of different type of sensors, the type sensors being one of of piezo-only sensors, accelerometer-only sensors and sensors having both accelerometer(s) and a piezo element.

Figure 8:
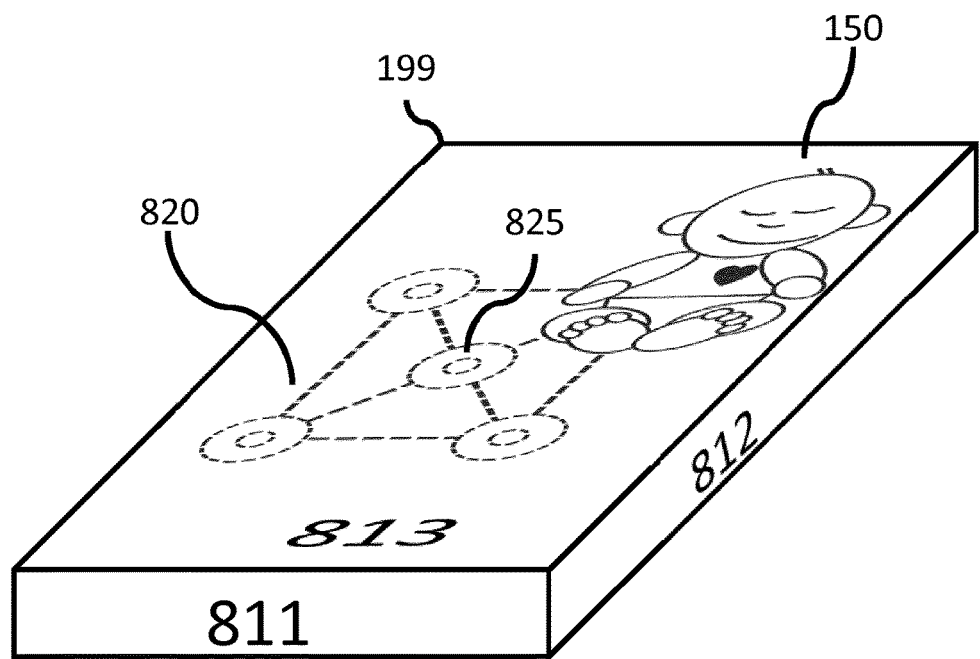
FIG. 8 illustrates a bird's-eye view of the mattress including the infant and the sleep monitoring device having five sensors.
Figure 8:
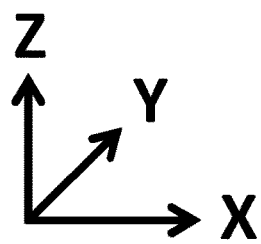

FIG. 8 illustrates a bird's-eye view of a mattress 199 including the infant 150 and the sleep monitoring device 820 having five sensors. The infant 150 and the mattress 199 are as in FIG. 2, whereas the device 820 is as in FIG. 3b. The mattress 199 has a bottom side 811, a lateral side 812 and a top surface 813. The infant 150 lies on the top surface 813, occluding one of the five sensors (note that the infant appears flat in this figure, but is assumed to have a non-flat shape nonetheless). The device 820 is preferably in or directly under the mattress. The mattress 199 as shown in FIG. 5 has three principal axes: X along the bottom side 811, Y along the lateral side 812, and Z orthogonal to the top surface 813.

In embodiments described above, the preferred direction of the sensors of device 820 is in the Z direction, e.g. most sensitive to pressure caused by 'pushing down' on the mattress 199. A sensor having its preferred direction in the Z-direction is optimally oriented for measuring pressure caused by breathing, body movements and weight of the infant, all generating pressure downwards in the Z-direction.

Yet, for measuring pressure waves caused by ballistic movements of a beating heart, a sensor is best oriented in the Y- or X-direction. The heart of the infant 15 generates ballistic movements primarily along the longitudinal axis of the infant, which corresponds to the Y-direction in FIG. 8. If the infant 150 changes its orientation so that its longitudinal axis aligns (i.e. parallel) with the X-direction, then the beating heart generates ballistic movements in the X-direction. In any case, the heart of the infant 150 which is lying on the mattress causes pressure waves primarily in the X-Y plane and to a substantially lesser extent in the Z-direction. A sensor having its preferred direction in the Z-direction will thus measure a smaller signal (having a worse signal-to-noise ratio) than a sensor with its preferred direction in the X- or Y-plane.

The device 820 may be adapted by orienting a central sensor 825 (of the five sensors) such that its preferred direction is in the Y direction. The central censor 825 is then better oriented to measure pressure waves caused by the ballistic movements of the infant's heart 150, according to its orientation as shown in FIG. 8. Alternatively, the device may also adapted by orienting the central sensor 825 such that its preferred direction is in the X-direction. The central sensor 825 is then better oriented to measure pressure waves caused by the ballistic movements, when the infant rotates it's orientation by, say, 90 degrees (or another substantial angle, e.g. 60 degrees).

The device 820 may also be adapted by orienting two sensors (rather than one sensor) in a different direction than the Z-direction. For example, a first sensor is oriented in the X-direction and a second sensor is oriented the Y-direction, so that at least one of the two sensors is not orthogonal to the primary direction of pressure waves caused by the ballistic movements. The remaining three sensors could then be used (by the localization function 120) to determine the position of the infant 150 on the mattress. Using the determined position of the infant 150, the magnitude attenuation factor ATT can then be determined (by the determining function 130) for one of the remaining three sensors, so that the magnitude of the heart signal at the position of the infant 150 can be determined (according to embodiments above). A heart signal from the first or second sensor can then be adapted by matching its magnitude to the determined magnitude of the heart signal at the infant's position. In this way, the heart signal has an improved signal-to-noise ratio because of being measured via the first and/or the second sensor, and has a correct magnitude because of the magnitude correction.

Note that a sensor need not be oriented precisely in one of the X, Y or Z directions, but may also be oriented in intermediate directions. For example, the two sensors in the previous paragraph may be oriented somewhere in between the Z-direction and a direction in the X-Y plane. Such an orientation would improve the sensitivity for measuring the heart signal, yet retain more sensitivity for measuring a breathing signal. In summary, the preferred direction of a sensor may be non-parallel to the Z-direction and have a significant directional component in the X-Y plane, but said preferred direction need not be precisely orthogonal to the Z-direction For example, an angle between said preferred direction and the Z-direction is larger than 5-to-10 degrees.

The current invention also includes a method for measuring a biophysical variable of a living-being, consistent with the sleep monitoring device 100. The method performs steps according to the localization function and the determining function of the sleep monitoring device 100. The method may be implemented as instructions of a computer program product that cause a processor to perform steps according to the method.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. Sleep monitoring device for measuring a biophysical variable of a living-being, the sleep monitoring device comprising sensors being at least two pressure sensors that are spatially arranged in a predefined planar geometry, the sensors being arranged for
    contacting a supporting layer for supporting the living-being while resting and
    generating respective sensor signals in response to pressure caused by the living-being via the supporting layer to the sensors,
        the sleep monitoring device further comprising a processing unit arranged for performing:
        (a) a localization function configured for
    determining a position (P0) of the living-being on the supporting layer relative to the sensors based on differences between the respective sensor signals by performing a multilateration procedure based on phase differences between the respective sensor signals or by performing a trilateration procedure based on magnitude differences between the respective sensor signals, and
        (b) a determining measurement function configured for
    determining a magnitude attenuation factor (ATT) based on the determined position of the living-being and a position (P1-P3) of one of the sensors, and
    determining the biophysical variable based on a sensor signal generated by the one of the sensors and the magnitude attenuation factor.

2. Sleep monitoring device as in claim 1, wherein the determining function is configured for selecting, from the sensors, one of the sensors generating a sensor signal having the largest magnitude among magnitudes of the respective sensor signals.

3. Sleep monitoring device as in claim 1, wherein
    the determining function is configured for determining the biophysical variable by
        determining multiple magnitude attenuation factors (ATT) based on the determined position of the living-being and on respective multiple positions (P1-P3) of respective multiple sensors of the sensors, and
        determining the biophysical variable based on respective multiple sensor signals generated by the respective multiple sensors and on the multiple magnitude attenuation factors.

4. Sleep monitoring device as in claim 1, wherein the determining function is configured for determining the biophysical physical variable being one of a breathing intensity rate, a heart-beat intensity, body weight, body movements, heart rate, and breathing rate.

5. Sleep monitoring device as in claim 1, wherein a preferred direction of a first sensor of the sensors is non-parallel to a surface normal vector (Z) of the predefined planar geometry, the preferred direction being a direction in which the first sensor responds most to pressure waves as compared to other directions than the preferred direction.

6. Sleep monitoring device as in claim 5, wherein a preferred direction of a second sensor of the sensors is non-parallel to the surface normal vector (Z) and to the preferred direction of the first sensor, the preferred direction of the second sensor being a direction in which the second sensor responds most to pressure waves as compared to other directions.

7. Sleep monitoring device as in claim 1, arranged for measuring the biophysical variable of a living-being being one of an adult human, an human infant or an animal.

8. Sleep monitoring device of as in claim 1, comprising (a) three sensors spatially arranged in the predefined planar geometry having a triangular shape, or (b) four sensors spatially arranged in the predefined planar geometry having a quadrilateral shape.

9. Sleep monitoring device as in claim 1, comprising five pressure sensors, (a) the five sensors being spatially arranged in the predefined planar geometry having a pentagon shape or (b) the first four of the five sensors being spatially arranged in a quadrilateral shape and the fifth sensor of the five sensors being inside the quadrilateral shape.

10. Sleep monitoring device as in claim 1, wherein
at least one of the sensors is a pressure sensor that is arranged to generate a sensor signal in response to pressure caused by the living-being by using at least one of (a) a piezo element and (b) an accelerometer.

11. Sleep monitoring device of as in claim 1, wherein the predefined planar geometry has a curved shape for fitting in the supporting layer having a curve shape, such that the curved shape of the predefined planar geometry follows the curved shape of the supporting layer.

12. Sleep monitoring device of as in claim 1, wherein the processing unit is further arranged to characterize a sleeping state of the living-being on the support layer based on a determination of the biophysical variable.

13. A sleep monitoring method by a sleep monitoring device for measuring a biophysical variable of a living-being the sleep monitoring device including at least two pressure sensors that are spatially arranged in a predefined planar geometry, the sensors being arranged for
contacting a supporting layer for supporting the living-being while resting,
generating respective sensor signals in response to pressure caused by the living-being via the supporting layer to the sensors,
the method comprising the steps of:
determining, by the sleep monitoring device, a position (P0) of the living-being on the supporting layer relative to the sensors based on differences between the respective sensor signals by performing a multilateration procedure based on phase differences between the respective sensor signals or by performing a trilateration procedure based on magnitude differences between the respective sensor signals,
determining, by the sleep monitoring device, a magnitude attenuation factor (ATT) based on the determined position of the living-being and a position (P1-P3) of one of the sensors, and
determining, by the sleep monitoring device, the biophysical variable based on a sensor signal generated by the one of the sensors and the magnitude attenuation factor.

14. A computer program product comprising instructions for causing a processor to perform the steps according to the method of claim 13.

15. Method of claim 13, further comprising:
characterizing, by the sleep monitoring device, a sleeping state of the living-being on the support layer based on a determination of the biophysical variable.

* * * * *